(12) United States Patent
Gomi

(10) Patent No.: US 8,279,439 B2
(45) Date of Patent: Oct. 2, 2012

(54) BIREFRINGENCE MEASURING DEVICE AND BIREFRINGENCE MEASURING METHOD

(75) Inventor: Kenji Gomi, Tokyo (JP)

(73) Assignee: Tokyo Denki University, Tokyo (JP)

( * ) Notice: Subject to any disclaimer, the term of this patent is extended or adjusted under 35 U.S.C. 154(b) by 676 days.

(21) Appl. No.: 12/439,441

(22) PCT Filed: Jun. 14, 2007

(86) PCT No.: PCT/JP2007/062019
§ 371 (c)(1),
(2), (4) Date: Sep. 9, 2009

(87) PCT Pub. No.: WO2008/026363
PCT Pub. Date: Mar. 6, 2008

(65) Prior Publication Data
US 2011/0134429 A1    Jun. 9, 2011

(30) Foreign Application Priority Data
Aug. 29, 2006   (JP) .................................. 2006-232380

(51) Int. Cl.
*G01J 4/00* (2006.01)
(52) U.S. Cl. ......................................................... 356/364
(58) Field of Classification Search .................. None
See application file for complete search history.

(56) References Cited

U.S. PATENT DOCUMENTS 6,157,448 A * 12/2000 Kowa et al. ................... 356/365
6,266,141 B1 * 7/2001 Morita ........................... 356/365

FOREIGN PATENT DOCUMENTS

| JP | 01-184444 A | 7/1989 |
| JP | 2006-071458 A | 3/2006 |
| JP | 2006-090820 A | 4/2006 |

OTHER PUBLICATIONS

International Preliminary Report on Patentability issued in PCT/JP2007/062019, mailed on Mar. 12, 2009 (with English translation).
Gomi, K. et al.; A New Measurement Technique of Low-Level Strain Retardation in Optoelectronic Materials; $1^{st}$ Electronic Systemintegration Technology Conference, vol. 1, pp. 257-262, Sep. 2006.

(Continued)

*Primary Examiner* — Tu Nguyen
(74) *Attorney, Agent, or Firm* — Foley & Lardner LLP

(57) ABSTRACT

The present invention is a birefringence measuring device that requires only three types of light intensity information and can measure birefringence characteristics of an object with a relatively inexpensive device configuration. One embodiment comprises a light source for emitting a light flux having a specific polarization state towards the object to be measured, an optical system for extracting each of light fluxes in predetermined three polarization direction; and, from the light flux having passed the object to be measured, a detector for detecting a light amount of each of the light fluxes in the predetermined three polarization directions extracted by the optical system, and a processor for calculating a size and an azimuth of the birefringence of the object to be measured. The processor may calculate the birefringence size and azimuth by assigning each of the light amounts of the light fluxes detected by the detector to a predetermined function expression.

20 Claims, 10 Drawing Sheets

OTHER PUBLICATIONS

Hobbs, J.W. et al.; A Novel Instrument for Transient Photoelasticity; *Experimental Mechanics*; vol. 43, No. 4, pp. 403-409, Dec. 2003.

International Search Report for International Application No. PCT/JP2007/062019 dated Jul. 17, 2007.

Kowa, H. et al.; Automated Birefringence Measurement Using Infrared Transverse Zeeman Laser; *Japanese Journal of Optics*, vol. 19, No. 7, pp. 464-471, Jul. 1990.

Malacara, D.; Optical Shop Testing; *Wiley Interscience*, pp. 502-551, 1992.

Roth, J.E. et al.; Simplified method for polarization-sensitive optical coherence tomography; *Optics Letters*, vol. 26, No. 14, pp. 1069-1071, Jul. 15, 2001.

Suzuki, H. et al.; Development of new equipment for birefringence measurement; *The Japan Society of Mechanical Engineers, Kouen Ronbushu*, vol. 1, pp. 879-880, Sep. 18, 2006.

Umezaki, E.; Present Situation of Digital Photoelasticity; *Experimental Dynamics*, vol. 4, No. 1, Mar. 2004.

Wikipedia "Photoelasticity," accessed at http://en.wikipedia.org/wiki/Photoelasticity , Dec. 7, 2011.

Zheng, T. and Danyluk, S., "Study of Stresses in Thin Silicon Wafers with Near-infrared Phase Stepping Photoelasticity," Journal of Materials Research, Jan. 2002, vol. 17, pp. 36-42.

Geiler, H.D., et al., "Photoelastic Characterization of Residual Stress in GaAs-wafers," Materials Science in Semiconductor Processing, vol. 9, Issues 1-3, Feb.-Jun. 2006, pp. 345-350.

"Modern Photoelastic Technology for Residual Stress Measurement in Glass," Laboratory of Photoelasticity, accessed at http://www.ioc.ee/plab/.

* cited by examiner

TABLE 1

| | BIREFRINGENCE AZIMUTH φ | | | | | | | |
|---|---|---|---|---|---|---|---|---|
| | -90 | — | -45 | — | 0 | — | 45 | — | 90 |
| $i_1 - \frac{i_2 + i_3}{2}$ | + | + | 0 | − | − | − | 0 | + | + |
| $i_2 - i_3$ | 0 | − | − | − | 0 | + | + | + | 0 |
| EXPRESSION 4 OR EXPRESSION 5 | γ OF EXPRESSION 4 | | γ OF EXPRESSION 5 | | γ OF EXPRESSION 4 | | γ OF EXPRESSION 5 | | γ OF EXPRESSION 4 |

FIG. 9

TABLE 2

| | | |
|---|---|---|
| SPECIFICATION AND TOLERANCE OF SAMPLE [nm] | 79.1±3.5 | 10.0±4.7 |
| PHASE DIFFERENCE MEASURED VALUE AND STANDARD DEVIATION BEFORE CORRECTION [nm]<br><br>(DECREASE RATE OF DEVIATION) ↓<br><br>AFTER CORRECTION [nm] | 77.6±3.24<br><br>(19.4%) ↓<br><br>77.5±2.61 | 10.5±2.62<br><br>(57.6%) ↓<br><br>10.3±1.11 |
| PHASE ANGLE MEASURED VALUE AND STANDARD DEVIATION BEFORE CORRECTION [°]<br><br>(DECREASE RATE OF DEVIATION) ↓<br><br>AFTER CORRECTION [°] | 10.1±1.23<br><br>(26.3%) ↓<br><br>10.0±0.906 | 10.1±4.31<br><br>(29.2%) ↓<br><br>10.0±3.05 |
| NUMBER OF MEASUREMENT TIMES | 110 | 111 |

PRIOR ART

BIREFRINGENCE MEASURING DEVICE AND BIREFRINGENCE MEASURING METHOD

CROSS-REFERENCE TO RELATED APPLICATIONS

The present application is a U.S. national stage application claiming priority to International Application No. PCT/JP2007/062019, filed on Jun. 14, 2007, which claims priority to Japanese Application No. 2006-232380, filed on Aug. 29, 2006, the entire contents of which are incorporated herein by reference in their entireties.

TECHNICAL FIELD

The present invention relates to a birefringence measuring device and a birefringence measuring method which are effective in measuring a size and an azimuth of micro birefringence such as a semiconductor crystal, an optical element, a flat display panel and the like, for example.

BACKGROUND ART

In the past, as a birefringence measuring device based on a phase shift method, a device introduced in a thesis "Current Situation of Digital Photoelasticity Method", by Eisaku Umezaki, Experimental Dynamics Vol. 4, No. 1, March 2004, FIGS. 6 and 7 and described in "A Novel Instrument for Transient Photoelasticity" by J. W. Hobbs, R. J. Greene and E. A. Patterson, Experimental Mechanics Vol. 43, No. 4, December 2003, pp. 403 to 409 is known.

FIG. 12 shows a configuration of such a prior-art birefringence measuring device, which is constituted by a light source 1, an expander 2, a polarizer 3, a ¼ wavelength plate 4 for circular polarized light, a sample stand 5 on which an object to be measured is placed, three beam splitters 6A to 6C for separation to four light fluxes, ¼ wavelength plates 7-1 to 7-4 installed for each of optical paths of the separated four light fluxes, analyzers 8-1 to 8-4, two-dimensional light intensity distribution measurement devices 9-1 to 9-4 such as a CCD camera, and a mirror 10 for directing the separated light fluxes to desired directions, as necessary. Actually, the two-dimensional intensity distribution measuring devices 9-1 to 9-4 are made into a single device so as to be configured to guide light to a two-dimensional intensity distribution measuring device 9 installed at a single location by using the mirror 10 and a pyramid mirror.

However, such a prior-art birefringence measuring device requires a light amount in four polarization directions for measuring birefringence characteristics of an object to be measured and also requires a ¼ wavelength plate on each of optical paths of the four polarization directions all the time, which is indispensable and raises a device cost, and an increase in the number of components leads to a problem of a lot of labor in an adjustment work.

On the other hand, the phase shift method is employed for measurement of wavefront aberration of a lens, and a 3-phase method is known in "Optical Shop Testing" by D. Malacara, Wiley Interscience, 1992. This publicly known 3-phase method does not use polarization. This method is an algorithm in which a single sine wave created by interference is observed by changing a condition temporally or spatially (using a spatial arrangement of a sensor, for example) so that as a result, the phase is shifted and a single unknown sine wave is acquired from the observed waveforms. Thus, it is not a proposal of an algorithm for acquiring a single polarization state converted from the circular polarization through birefringence of a sample using three polarization directions.

DISCLOSURE OF INVENTION

The present invention was made in view of the above prior-art technical problems and has an object to provide a birefringence measuring device and a birefringence measuring method which requires only three types of light intensity information and thus, can measure birefringence characteristics of an object to be measured with a relatively inexpensive device configuration.

An aspect of the present invention is a birefringence measuring device having a light source that emits a light flux having a specific polarization state to the object to be measured, an optical system for extracting each light flux in predetermined three polarization directions from the light flux having passed the object to be measured, light-amount detecting means for detecting a light amount of each of the light fluxes in the predetermined three polarization directions extracted by the optical system, and birefringence amount measuring means for calculating a size of birefringence of the object to be measured and an azimuth thereof by assigning each light amount of the detected light fluxes detected by the light-amount detecting means to a predetermined function expression.

In the above birefringence measuring device, the optical system can extract each light flux in the predetermined three polarization directions by switching and installing three types of analyzers transmitting only each of the predetermined three polarization directions sequentially on the optical path.

Also, in the above birefringence measuring device, the optical system can have light-flux dividing means for dividing the light flux having passed the object to be measured into three light fluxes to be detected in a state where the polarization state is preserved and three analyzers for extracting a light flux in a predetermined polarization direction from each of the three light fluxes to be detected at the same time.

With the birefringence measuring device of the present invention, a light flux having a specific polarization state is emitted from a light source to an object to be measured, a light flux each in the predetermined three polarization directions is extracted by the optical system from the light flux having passed the object to be measured, a light amount of each light flux in the predetermined three polarization directions extracted by the optical system is detected by the light-amount detecting means, and each light amount of the detected light flux is assigned to a predetermined function expression by the birefringence amount calculating means so as to calculate a size and an azimuth of the birefringence of the object to be measured. As a result, the birefringence measuring device of the present invention requires only three optical systems and does not require installation of a ¼ wavelength plate in front of the analyzer in each polarization direction in order to extract each light flux in the predetermined three polarization directions and thus, the birefringence characteristics of the object to be measured can be measured by a simplified device configuration.

Another aspect of the present invention is a birefringence measuring method in which a light flux having a specific polarization state is emitted to an object to be measured on a sample stand, the light flux having passed the object to be measured is made to pass through an optical system so as to have a light flux each in predetermined three polarization directions extracted, a light amount of each light flux in the predetermined three polarization directions extracted by the optical system is detected, and the light amount of each light flux in the predetermined three polarization directions is assigned to a predetermined function expression so that a size of the object to be measured and an azimuth thereof are calculated.

The above birefringence measuring method may be so configured that axes of 45°, 0°, 90°, respectively, are set as the predetermined three polarization directions, and when $i_1$, $i_2$, $i_3$ are obtained as light amounts in each axial direction, a size $\gamma$ and an azimuth $\phi$ of birefringence of the object to be measured are determined by the following expressions:

$$\phi = \frac{1}{2}\tan^{-1}\left(\frac{i_2 - i_3}{-2i_1 + i_2 + i_3}\right) \quad \text{[Expression A1]}$$
$$\gamma = \sin^{-1}\left(\frac{-2i_1 + i_2 + i_3}{(i_2 + i_3)\cos 2\phi}\right)$$

or $$\phi = \frac{1}{2}\tan^{-1}\left(\frac{i_2 - i_3}{-2i_1 + i_2 + i_3}\right) \quad \text{[Expression A2]}$$
$$\gamma = \sin^{-1}\left(\frac{i_2 - i_3}{(i_2 + i_3)\sin 2\phi}\right)$$

In the birefringence measuring method of the present invention, the birefringence measuring device employed for reduction to practice thereof requires only three optical systems and does not require installation of a ¼ wavelength plate in front of an analyzer in each polarization direction for extracting each light flux in the predetermined three polarization directions and thus, the birefringence characteristics of the object to be measured can be measured by a simplified device configuration.

Also, in the above birefringence measuring method, a size and an azimuth of true birefringence of the object to be measured from which an error of a measurement system is eliminated can be acquired with the following method:

That is, (a) A target object to be measured or an arbitrary object to be measured is used as a test object to be measured, and the test object to be measured is rotated around an optical axis of a light source at least 180° so as to measure the size and the azimuth of the birefringence, a relation between a fluctuation tendency of the birefringence size and the birefringence azimuth of the test object to be measured is acquired, a birefringence size $\gamma'$ and an azimuth $\phi'$ causing the fluctuation tendency are estimated, and the birefringence offsetting it is set as compensation birefringence r';

(b) the compensation birefringence r' is vector-synthesized with the measurement result of the test object to be measured so as to acquire the relation between the fluctuation tendency of the size and the azimuth of the birefringence again, and a standard deviation of the birefringence size of the test object to be measured from the relation;

(c) by changing the birefringence size $\gamma'$ and the azimuth $\phi'$ as appropriate, the compensation birefringence r' acquired from the size $\gamma'$ and the azimuth $\phi'$ of the birefringence after the change is vector-synthesized again with the measurement result of the test object to be measured so as to re-acquire the relation between the fluctuation tendency of the size and the azimuth of the birefringence, and the standard deviation of the size of the birefringence of the test object to be measured is acquired from the relation;

(d) the processing in the above (c) is repeated so as to search the size $\gamma'$ and the azimuth $\phi'$ of the birefringence where the standard deviation of the size of the birefringence of the test object to be measured is the minimum, and the compensation birefringence obtained as the result of the search is set as final compensation birefringence r'';

(e) the final compensation birefringence r'' obtained by the processing in the above (d) is set as a calibration value;

(f) the size $\gamma$ and the azimuth $\phi$ of the birefringence of the target object to be measured are measured, and the birefringence r is acquired from the measurement result; and (g) the final compensation birefringence r'' obtained by the processing in the above (d) is vector-synthesized with the birefringence r obtained by the processing in the above (f) so as to obtain compensated birefringence $r_{real}$. Vector components of the compensated birefringence $r_{real}$ are the size $\gamma_{real}$ and the azimuth $\phi_{real}$ of the true birefringence of the object to be measured from which a tolerance of the measurement system is eliminated.

According to the birefringence measuring device of the present invention, the device requires only three optical systems and does not require installation of a ¼ wavelength plate in front of an analyzer in each polarization direction in order to extract each light flux in the predetermined three polarization directions and thus, the birefringence characteristics of the object to be measured can be measured with a simplified device configuration.

Also, according to the birefringence measuring method of the present invention, the birefringence characteristics of the object to be measured can be measured by a birefringence measuring device with a simple configuration.

Moreover, in the birefringence measuring method of the present invention, first, the compensation birefringence of the measurement system is acquired by using a test object to be measured, the compensation vector is vector-synthesized with a measured value vector acquired from the birefringence measured value of the object to be measured, and the size and the azimuth of the true birefringence of the object to be measured from which an error of the measurement system is eliminated using a vector having the standard deviation to be the minimum is acquired so that the birefringence measurement with high accuracy and from which an error caused by the tolerance of the measurement system is eliminated can be realized.

BRIEF DESCRIPTION OF THE DRAWINGS

FIG. 9 is a table 2 of the measurement results of a phase difference and an azimuth of a sample of 79 nm, 10 nm according to the embodiment of the present invention.

BEST MODE FOR CARRYING OUT THE INVENTION

Embodiments of the present invention will be described below in detail referring to the attached drawings.

Figure 1:
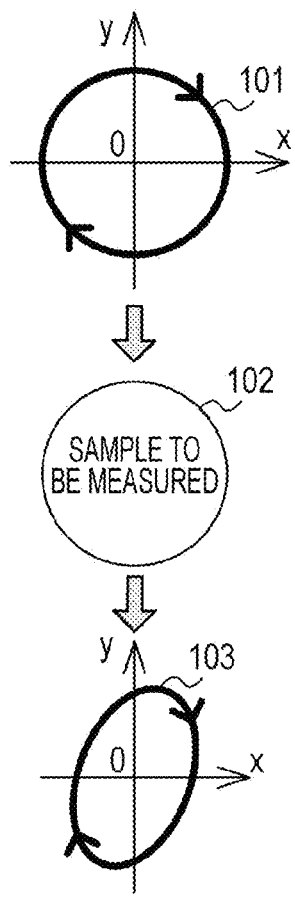
FIG. 1 is an explanatory diagram of a birefringence measurement principle of the present invention.
Figure 2:
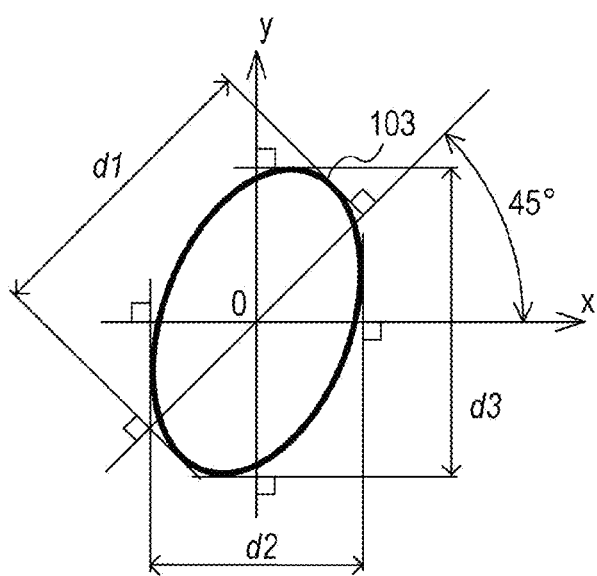
FIG. 2 is an explanatory diagram illustrating an example of a reference face trace of an elliptical polarization light and a relation among three dimensions $d_1$, $d_2$, $d_3$ determining the trace.

First, a principle of a birefringence measurement technique of the present invention will be described. In this birefringence measurement, a circular polarization light 101 is made to enter a sample 102 as shown in FIG. 1, and by obtaining knowledge of an ellipticity of an elliptical polarization light 103 emitted from the sample 102 and an azimuth of a long axis, a micro birefringence and the azimuth of the sample are measured. In general, an ellipse having a midpoint of two focal points that matches an origin of a coordinate system is determined uniquely if three dimensions $d_1$, $d_2$, $d_3$ as shown in FIG. 2, for example, are specified. In order to obtain the three dimensions $d_1$, $d_2$, $d_3$, it is only necessary to match a principal-axis azimuth of an analyzer (photodetector) with the azimuth of each dimension and to measure intensity of the light transmitted through the analyzer. Then, the "three dimension" $d_1$, $d_2$, $d_3$ in the present invention are described as "three light intensities" $i_1$, $i_2$, $i_3$. In general, the respective azimuths of the three light intensities $i_1$, $i_2$, $i_3$ may be arbitrary as long as they are different from each other. However, in view of rationality of calculation in the present invention, the three azimuths shall be 0°, 45°, and 90° as shown in FIG. 2.

A relation among the three light intensities $i_1$, $i_2$, $i_3$, the birefringence phase difference γ of the sample, and a phase advance axis azimuth φ thereof can be described as follows using the calculation method of Jones matrix:

$$i_1 = \frac{i_0^2}{2}(1 - \cos 2\phi \sin \gamma)$$ [Expression 1]

$$i_2 = \frac{i_0^2}{2}(1 + \sin 2\phi \sin \gamma)$$

$$i_3 = \frac{i_0^2}{2}(1 - \sin 2\phi \sin \gamma)$$

where, $i_0$ is an amplitude of the light transmitted through a polarizer. When this expression is solved for φ and γ, the solution is as follows:

$$\phi = \frac{1}{2}\tan^{-1}\left(\frac{i_2 - i_3}{-2i_1 + i_2 + i_3}\right)$$ [Expression 2]

$$\gamma = \sin^{-1}\left(\frac{-2i_1 + i_2 + i_3}{(i_2 + i_3)\cos 2\phi}\right)$$

or $$\phi = \frac{1}{2}\tan^{-1}\left(\frac{i_2 - i_3}{-2i_1 + i_2 + i_3}\right)$$ [Expression 3]

$$\gamma = \sin^{-1}\left(\frac{i_2 - i_3}{(i_2 + i_3)\sin 2\phi}\right)$$

Here, the expression 2 and the expression 3 can be used separately according to a value of φ, which will be described later. Therefore, the birefringence phase difference γ of the sample and the phase advance axis azimuth φ can be uniquely determined from the measured three light intensities $i_1$, $i_2$, $i_3$, and this particularly means that the polarization state of the sample can be determined.

(First Embodiment)

Figure 3:
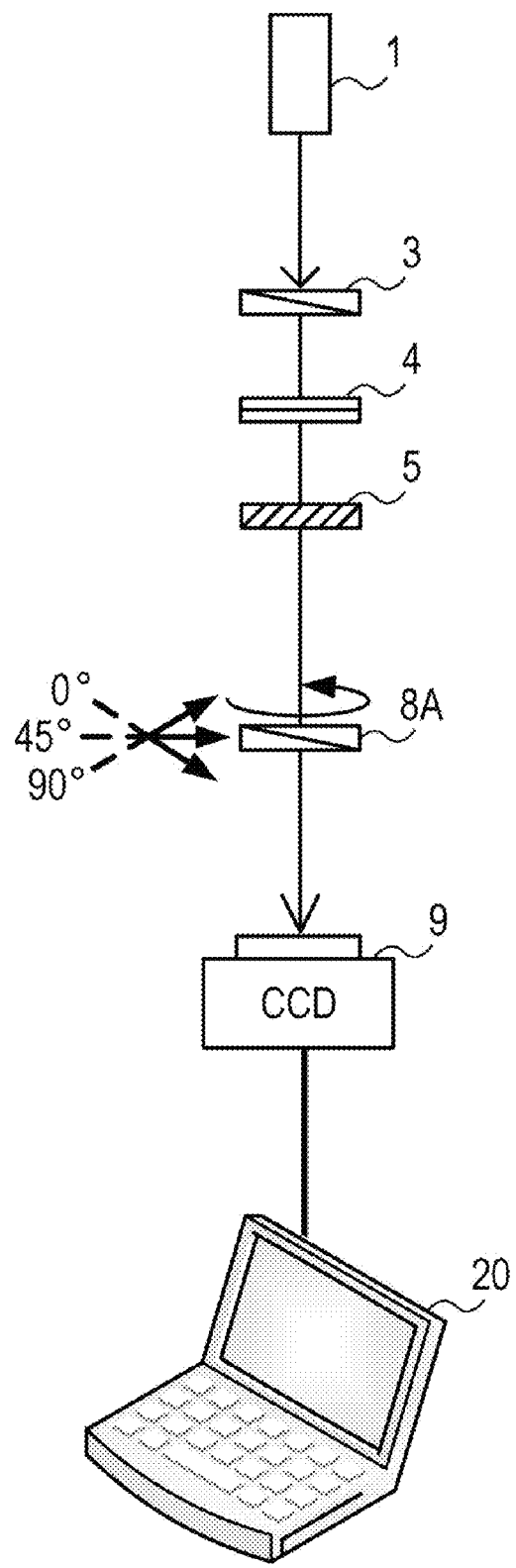
FIG. 3 is a block diagram of a birefringence measuring device of a first embodiment of the present invention.

FIG. 3 shows a birefringence measuring device of a first embodiment of the present invention. As the basic configuration, the birefringence measuring device comprises a laser light source 1, which is a light source of a monochromatic light, a polarizer 3 for aligning a light flux from the laser light source 1 to a specific polarization axis, a ¼ wavelength plate 4 for circularly polarizing the light flux having passed the polarizer 3, a sample stand 5 on which an object to be measured is installed, a rotating analyzer 8A for analyzing the light flux having passed the object to be measured on the sample stand 5 by stopping at 0° axis, 45° axis, 90° axis as the predetermined three axis directions, respectively, a CCD camera 9 as a light receiving element for receiving the light flux having passed the rotating analyzer 8A and taking out a light amount (light intensity), and a computer 20 in which outputs $i_1$, $i_2$, $i_3$ of the CCD camera 9 are inputted and birefringence characteristics of the object to be measured are calculated by calculation processing according to a predetermined program, which will be described later. The light source 1 is not limited to a laser light source as long as it is a monochromatic light source. Also, it does not have to be a monochromatic light source but it may be made close to monochromatic using an appropriate filter. Moreover, the CCD camera as a light receiving element employed herein and after is not limited to the CCD camera but any element that can measure light receiving intensity may be employed. However, in order to measure multiple spots in a lump sum such as 250 thousand spots of each axis at a time, for example, the CCD camera 9 may be employed.

Subsequently, a birefringence measuring method by the birefringence measuring device with the above configuration will be described. For the laser light source 1, a helium neon laser is used, for example, and laser with a wavelength of 632.8 nm is emitted. For the wavelength of the light source, a wavelength that an object to be measured transmits is chosen such as infrared laser if the object to be measured is a semiconductor crystal, for example.

A circular polarized light flux is obtained by aligning the polarization direction of the laser light by the polarizer 3 and by having the light passed through the ¼ wavelength plate 4. Then, the circular polarized light flux is irradiated to the object to be measured on the sample stand 5. The light having passed the object to be measured is applied with elliptical polarization according to stress distribution of the object to be measured. The elliptically polarized light flux enters a rotating analyzer 8A which can be fixed to each of the predetermined three axis directions.

The rotating analyzer 8A can be fixed at three axes of 0°, 45°, 90° axes, and by having the light flux having been elliptically polarized enter in a state fixed to the 0° axis, first, and by having the light flux in the 0-axis direction pass and reach the CCD camera 9. The CCD camera 9 receives the light flux from the rotating analyzer 8A and outputs a signal $i_2$ according to the intensity to the computer 20.

Subsequently, the rotating analyzer 8A is fixed to the 45° axis and the light flux having been elliptically polarized again is made to enter in that state and the light flux in the 45° axis direction is made to pass and reach the CCD camera 9 as the light receiving element. The CCD camera 9 receives the light flux from the rotating analyzer 8A and outputs a signal $i_1$ according to the intensity to the computer 20.

Similarly, the rotating analyzer 8A is fixed to the 90° axis and the light flux having been elliptically polarized again is made to enter in that state and the light flux in the 90° axis direction is made to pass and reach the CCD camera 9 as the light receiving element. The CCD camera 9 receives the light flux from the rotating analyzer 8A and outputs a signal $i_3$ according to the intensity to the computer 20.

In the computer 20, using the light intensity $i_1$ of the 45° axis, the light intensity $i_2$ of the 0° axis, and the light intensity $i_3$ of the 90° axis from the CCD camera 9, the following expression 4 or expression 5 is calculated so as to calculate the size γ and the azimuth φ of the birefringence of the object to be measured:

$$\phi = \frac{1}{2}\tan^{-1}\left(\frac{i_2 - i_3}{-2i_1 + i_2 + i_3}\right) \quad \text{[Expression 4]}$$

$$\gamma = \sin^{-1}\left(\frac{-2i_1 + i_2 + i_3}{(i_2 + i_3)\cos 2\phi}\right)$$

$$\phi = \frac{1}{2}\tan^{-1}\left(\frac{i_2 - i_3}{-2i_1 + i_2 + i_3}\right) \quad \text{[Expression 5]}$$

$$\gamma = \sin^{-1}\left(\frac{i_2 - i_3}{(i_2 + i_3)\sin 2\phi}\right)$$

The light intensities $i_1$, $i_2$, $i_3$ obtained in the present embodiment are described in the following expression 6:

$$i_1 = \frac{i_0^2}{2}(1 - \cos 2\phi \sin \gamma) \quad \text{[Expression 6]}$$

$$i_2 = \frac{i_0^2}{2}(1 + \sin 2\phi \sin \gamma)$$

$$i_3 = \frac{i_0^2}{2}(1 - \sin 2\phi \sin \gamma)$$

Here, $i_0$ is an amplitude of the light flux after passing through the polarizer 3, γ is the size of the birefringence existing in the object to be measured, and φ is the azimuth of the birefringence existing in the object to be measured. When the expression 6 is solved for φ, γ, the following expression 7 and expression 8 are obtained:

$$\phi = \frac{1}{2}\tan^{-1}\left(\frac{i_2 - i_3}{-2i_1 + i_2 + i_3}\right) \quad \text{[Expression 7]}$$

$$\gamma = \sin^{-1}\left(\frac{-2i_1 + i_2 + i_3}{(i_2 + i_3)\cos 2\phi}\right)$$

$$\phi = \frac{1}{2}\tan^{-1}\left(\frac{i_2 - i_3}{-2i_1 + i_2 + i_3}\right) \quad \text{[Expression 8]}$$

$$\gamma = \sin^{-1}\left(\frac{i_2 - i_3}{(i_2 + i_3)\sin 2\phi}\right)$$

The expression 7 and expression 8 are the same as the above expression 4 and expression 5. Thus, by inputting the light intensities $i_1$, $i_2$, $i_3$ and calculating the expression 4 or expression 5 by means of the computer 20, the size γ of the birefringence existing in the object to be measured and the azimuth φ of the birefringence existing in the object to be measured can be calculated.

Figures 4, 5:
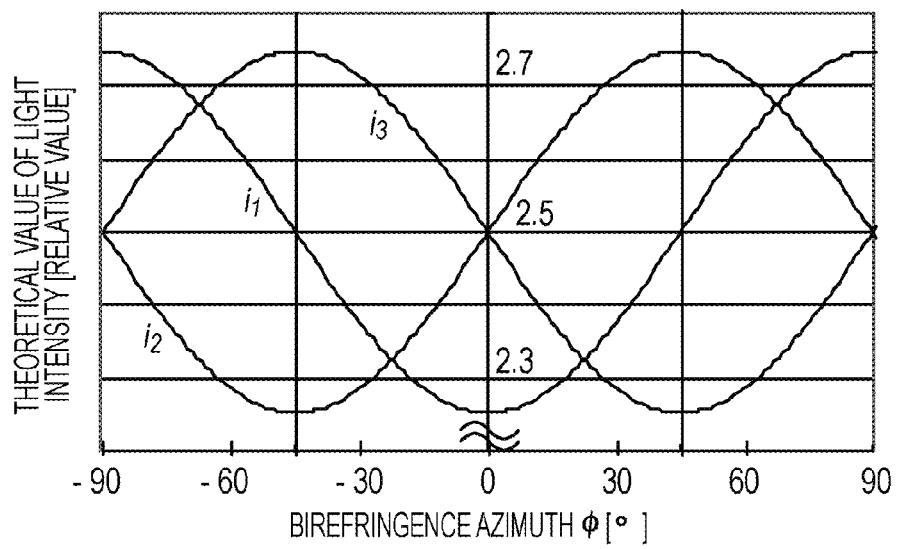
FIG. 4 is a graph comparing theoretical values of light intensity on each of three axes of a light source used in the birefringence measuring device of the first embodiment of the present invention.
FIG. 5 is a table 1 illustrating application cases between an expression 4 and an expression 5 in a birefringence measuring method by the birefringence measuring device of the present invention.

Details of which to use the expression 4 or expression 5 are as follows. FIG. 4 shows a theoretical calculation result of the light intensities $i_1$, $i_2$, $i_3$ obtained from the object to be measured having a birefringence phase difference of 10 nm, for example. The longitudinal axis indicates relative intensities of the light intensities $i_1$, $i_2$, $i_3$ and the lateral axis indicates the azimuth φ of the birefringence of the object to be measured. When φ=±45°, $i_1 = (i_2 + i_3)/2$ from FIG. 4, and therefore, the right side of the expression 4 becomes indefinite, and thus, γ is acquired by the expression 5 instead of γ in the expression 4.

The equations of φ in the expression 4 and expression 5 are arctangent functions. Therefore, the range of values is −45°≦φ≦45°, which is not all the values that φ can actually take. Thus, in this embodiment, in order to associate with the value that φ can actually take, combination of values of $i_1 − (i_2+i_3)/2$ and $(i_2−i_3)$ shown in Table 1 of FIG. 5 is used. Which to use, γ in the expression 4 or γ in the expression 5, is also described together in Table 1.

Figure 12:
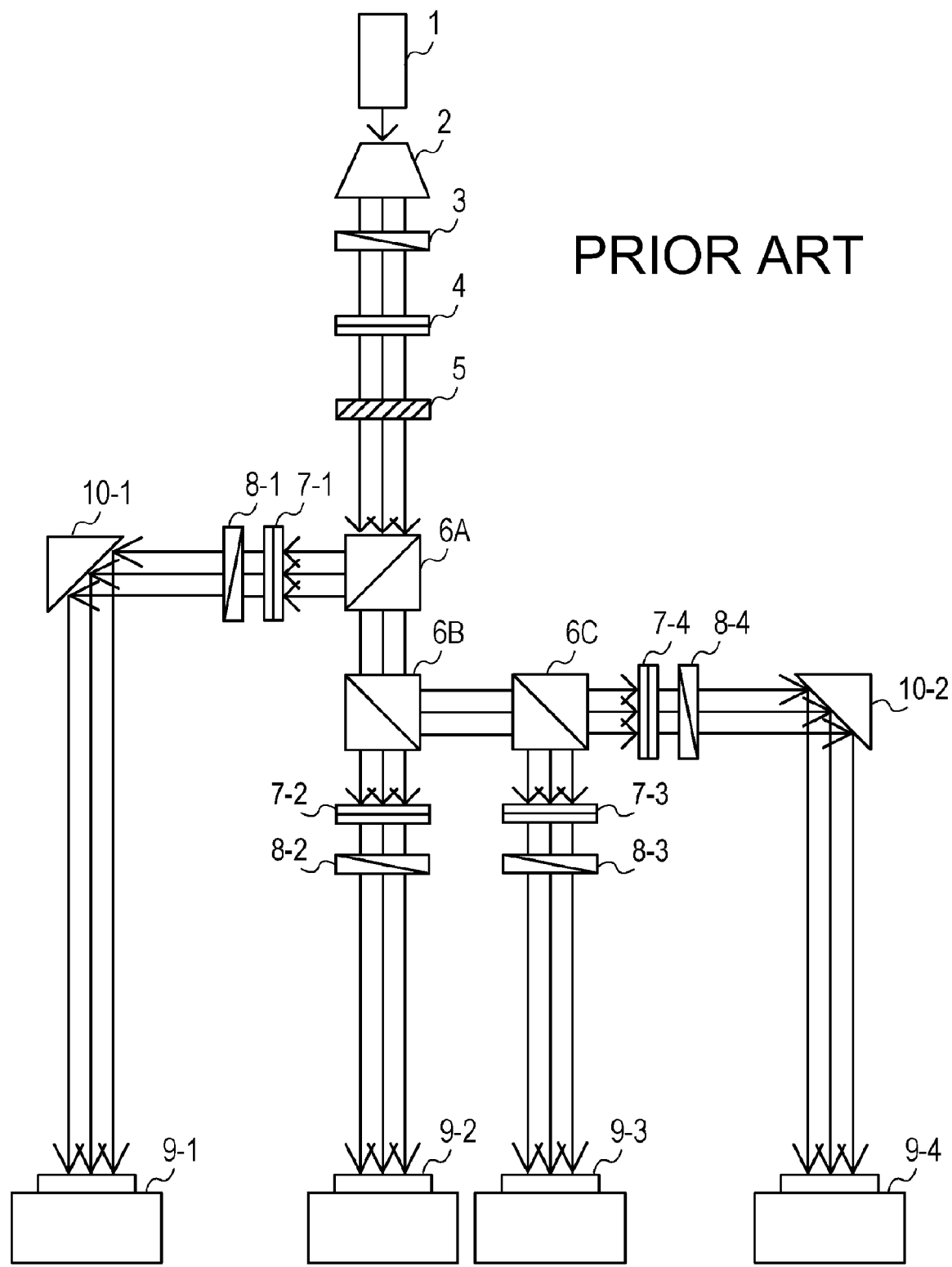
FIG. 12 is a block diagram of a birefringence measuring device of a prior-art example.

According to the birefringence measuring device and the method of this embodiment, since the light amounts (light intensities) of the light flux in three axis directions can be measured by a single optical system, and moreover, the ¼ wavelength plate is not needed at the sample stand 5 and after, the size of micro birefringence and the azimuth existing in the object to be measured can be measured with accuracy with an extremely simple device configuration as compared with the prior-art device shown in FIG. 12.

Figure 6:
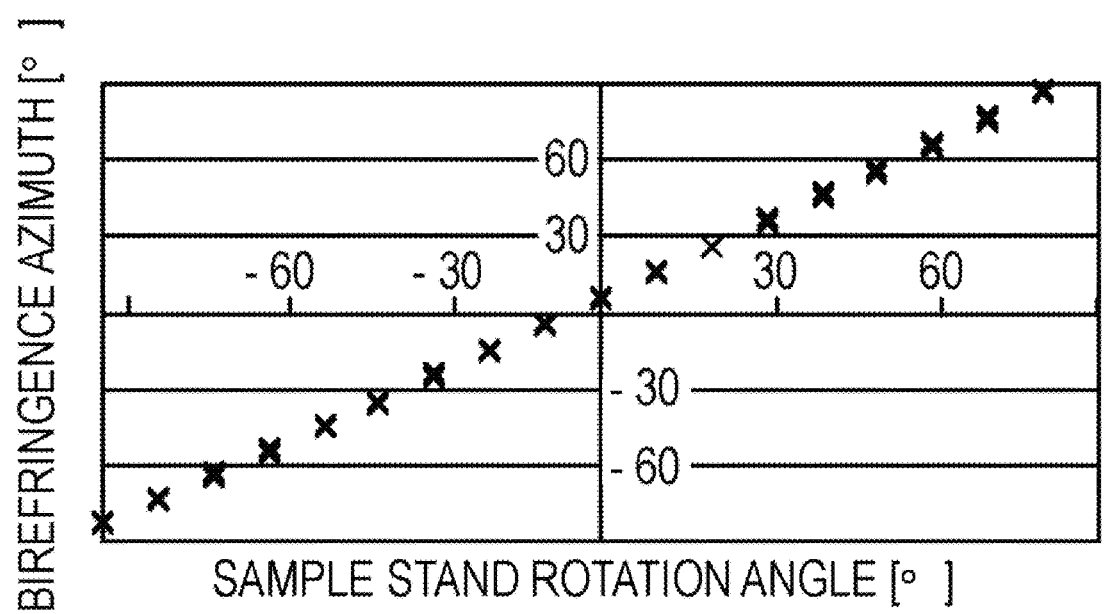
FIG. 6 is a graph of measurement results of a birefringence azimuth by the birefringence measuring device according to the first embodiment of the present invention.

A graph in FIG. 6 shows a measurement result of the birefringence azimuth. From the graph, it is known that the birefringence azimuth of the object to be measured can be measured with accuracy.

(Second Embodiment)

A birefringence measuring device of a second embodiment of the present invention will be described using FIG. 7. The birefringence measuring device of this embodiment can measure multiple spots of an object to be measured such as 250 thousand spots, for example, in a lump sum at once in a short measurement time by measuring the light intensities (light amounts) in the three axis directions at the same time and measures the birefringence characteristics of the whole surface even of an object to be measured with a wide area in a short time.

Figure 7:
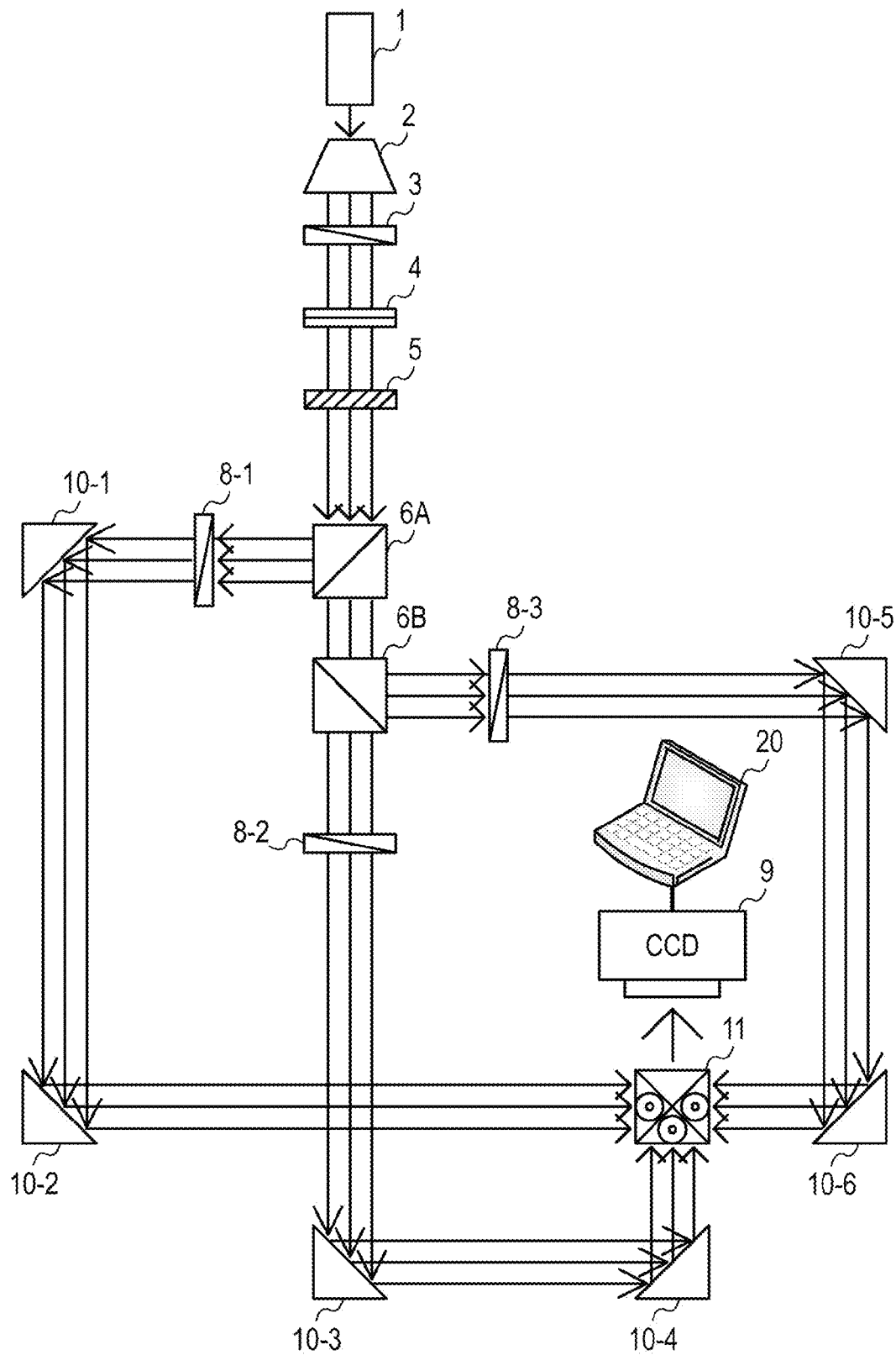
FIG. 7 is a block diagram of the birefringence measuring device according to a second embodiment of the present invention.

As shown in FIG. 7, the birefringence measuring device of this embodiment comprises the laser light source 1 as a monochromatic light source, the expander 2, the polarizer 3, the ¼ wavelength plate 4 for circular polarization, the sample stand 5 on which the object to be measured is placed, two beam splitters 6A, 6B for separating the light into three light fluxes, analyzers 8-1 to 8-3 for having polarization light in the axial directions of 0°, 45°, 90°, respectively, pass on optical paths of the separated three light fluxes, the CCD camera 9 for measuring two-dimensional light intensity distribution, mirrors 10-1 to 10-6 arranged at appropriate spots on the optical path for directing the three separated light fluxes in a direction of the CCD camera 9, a quadrangular pyramid mirror 11 for receiving each of the light fluxes in the three polarization directions and emitting the light toward the CCD camera 9 at a single spot, and the computer 20 in which light-amount detection signals $i_1$, $i_2$, $i_3$ of the CCD camera 9 are inputted and the size γ and the azimuth φ of the birefringence of the object to be measured are calculated on the basis of predetermined arithmetic expression similarly to the first embodiment.

Subsequently, the birefringence measuring method by the birefringence measuring device with the above configuration will be described. For the laser light source 1, similarly to the first embodiment, a laser of 632.8 nm is emitted using a helium neon laser, for example. Then, after the laser light flux is expanded by the expander 2, the light is made to enter the polarizer 3. The polarization direction of the light flux is aligned by the polarizer 3 and then, the light is passed through the ¼ so as to obtain a circular polarized light flux is obtained. Then, the circular polarized light flux is irradiated to the object to be measured on the sample stand 5. The light having passed the object to be measured is applied with elliptical polarization according to the stress distribution of the object to be measured. The light flux applied with the elliptical polarization is separated into three light fluxes by the two beam splitters 6A, 6B. Each of the light fluxes separated by the beam splitters 6A, 6B is made to enter each of the analyzers 8-1 to 8-3 installed on each optical path.

The analyzers 8-1 to 8-3 have the light in the three axes of 0° 45°, 90° axis directions pass, respectively. The light fluxes having passed each of the analyzers 8-1 to 8-3, respectively, are reflected by the mirrors 10-1 to 10-6 installed on the optical path and made to enter each of three side faces of the quadrangular pyramid mirror 11. The light flux of each axis applied with flection reflex at the quadrangular pyramid mirror 11 is made to enter the CCD camera 9 and converted to electric signals corresponding to light intensity of each axis and then, outputted as the light intensity (light amount) signals $i_1$, $i_2$, $i_3$ of the three axis directions to the computer 20.

In the computer 20, similarly to the first embodiment, the expression 4 or expression 5 is calculated using the light intensity $i_1$ of the 45° axis, the light intensity $i_2$ of the 0° axis, and the light intensity $i_3$ of the 90° axis from the CCD camera 9, the size $\gamma$ and the azimuth $\phi$ of the birefringence in the object to be measured are calculated.

The calculation processing by means of the computer 20 is in common to that in the first embodiment, and the expression 4 and expression 5 are used separately according to the value of $\phi$. That is, when $\phi=\pm 45°$, $i_1=(i_2+i_3)/2$ from FIG. 4 and therefore, the right side of the expression 4 becomes indefinite, and thus, $\gamma$ is acquired by the expression 5 instead of $\gamma$ in the expression 4.

Also, in this embodiment, in order to associate with the value that $\phi$ can actually take, combination of values of $i_1-(i_2+i_3)/2$ and $(i_2-i_3)$ shown in Table 1 in FIG. 5 is used.

According to the birefringence measuring device and the method of this embodiment, since the light amounts (light intensities) of the light fluxes in three axis directions can be measured at the same time, and moreover, the ¼ wavelength plate is not needed at the sample stand 5 and after, and the size of micro birefringence existing in the object to be measured and the azimuth can be measured with accuracy using a device with a simple configuration provided with only two units, which is one unit minus the prior one, of beam splitters.

The predetermined three axis directions in the present invention are not limited to the exemplification in the embodiments but it may be so configured that three axis directions with three different angles are specified and analyzers are installed in the respective directions so as to realize the similar birefringence measurement. Also, the quadrangular pyramid mirror is employed as necessary, and another means may be employed instead of the mirror.

Moreover, in the birefringence measuring method using the birefringence measuring device of each of the above embodiments, a size $\gamma_{real}$ and an azimuth $\phi_{real}$ of the birefringence with higher accuracy of an object to be measured from which an error in the measurement system is eliminated can be obtained by means of the following calibration:

(a) A target object to measured or an arbitrary object to be measured is used as a test object to be measured, and the test object to be measured is rotated around an optical axis of a light source at least 180° so as to measure the size and the azimuth of the birefringence, a relation between a fluctuation tendency of the birefringence size and the birefringence azimuth of the test object to be measured is acquired, a birefringence size $\gamma'$ and an azimuth $\phi'$ causing the fluctuation tendency are estimated, and the birefringence offsetting it is set as compensation birefringence $r'$.

(b) The compensation birefringence $r'$ is vector-synthesized with the measurement result of the test object to be measured so as to acquire the relation between the fluctuation tendency of the size and the azimuth of the birefringence again, and a standard deviation of the birefringence size of the test object to be measured from the relation.

(c) By changing the birefringence size $\gamma'$ and the azimuth $\phi'$ as appropriate, the compensation birefringence $r'$ acquired from the size $\gamma'$ and the azimuth $\phi'$ of the birefringence after the change is vector-synthesized again with the measurement result of the test object to be measured so as to re-acquire the relation between the fluctuation tendency of the size and the azimuth of the birefringence, and the standard deviation of the size of the birefringence of the test object to be measured is acquired from the relation.

(d) the processing in the above (c) is repeated so as to search the size $\gamma'$ and the azimuth $\phi'$ of the birefringence where the standard deviation of the size of the birefringence of the test object to be measured is the minimum, and the compensation birefringence obtained as the result of the search is set as final compensation birefringence $r''$.

(e) The final compensation birefringence $r''$ obtained by the processing in the above (d) is set as a calibration value.

(f) The size $\gamma$ and the azimuth $\phi$ of the birefringence of the actual target object to be measured are measured, and the birefringence $r$ is acquired from the measurement result.

(g) The final compensation birefringence $r''$ obtained by the processing in the above (d) is vector-synthesized with the birefringence $r$ of the actual object to be measured obtained by the processing in the above (f) so as to obtain compensated birefringence $r_{real}$. Vector components of the compensated birefringence $r_{real}$ obtained by this processing are the size $\gamma_{real}$ and the azimuth $\phi_{real}$ of the true birefringence of the object to be measured from which a tolerance of the measurement system is eliminated.

[Embodiment]

Figure 8:
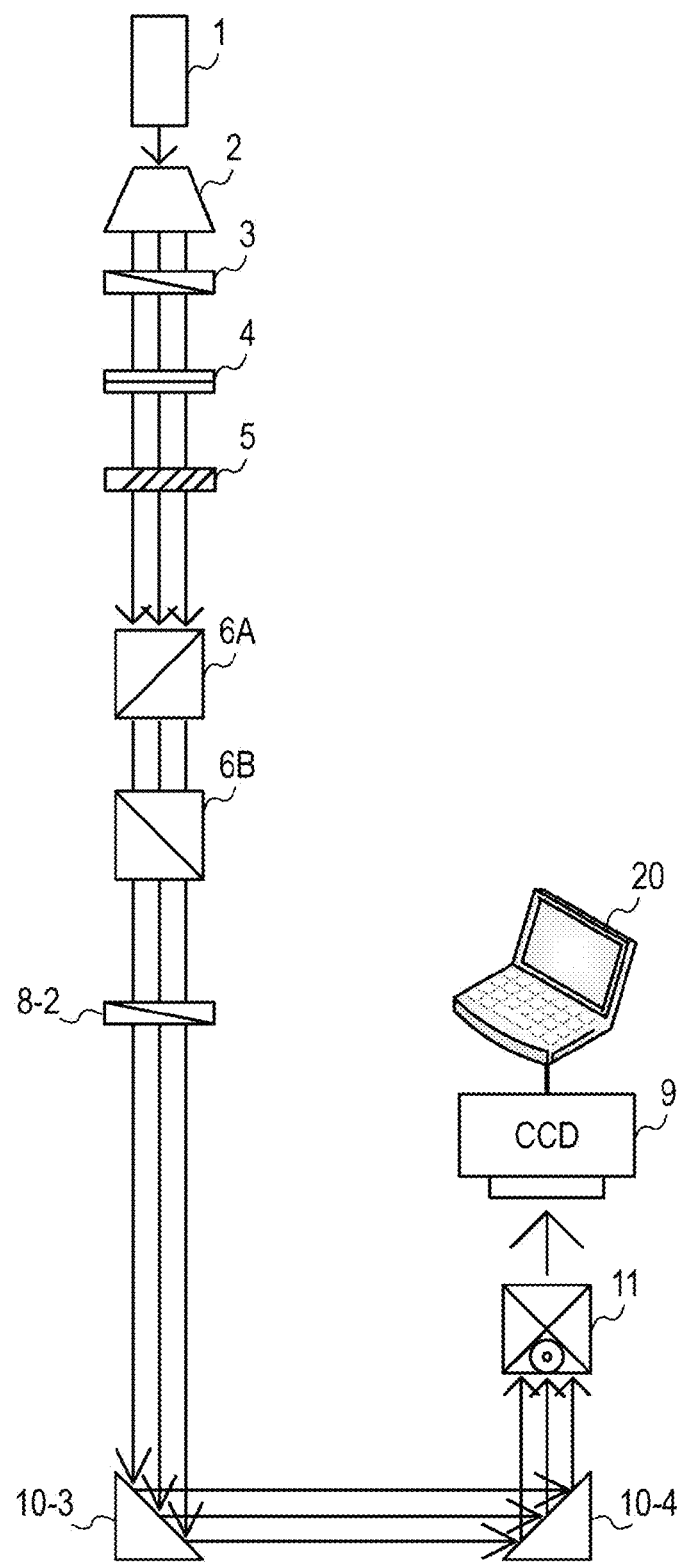
FIG. 8 is a block diagram of the birefringence measuring device according to an embodiment of the present invention.

An embodiment of the birefringence measuring device of the present invention will be described. The birefringence measuring device with the configuration shown in FIG. 8 is used. The birefringence measuring device of this embodiment is constituted by the laser light source 1 with a wavelength $\lambda=632.8$ nm, the polarizer 3 for aligning the light flux from the laser light source 1 to a specific polarization axis, the ¼ wavelength plate 4 for circularly polarizing the light flux having passed the polarizer 3, the sample stand 5 on which an object to be measured is placed, two units of the beam splitters 6A, 6B for separating the light flux having passed the object to be measured on the sample stand 5 to three directions, the analyzer 8 for analyzing the light flux in one direction having passed the beam splitters 6A, 6B, the mirrors 10-3, 10-4 for changing the direction of the light flux having passed the analyzer 8 by means of reflection, the quadrangular pyramid mirror 11 for receiving the light flux reflected by the mirror 10-4 and emitting it in a predetermined direction, the CCD camera 9 for measuring and taking out a light amount (light intensity) of the light flux emitted from the quadrangular pyramid mirror 11, and the computer 20 in which outputs $i_1$, $i_2$, $i_3$ of the CCD camera 9 are inputted and birefringence characteristics of the object to be measured are calculated by calculation processing according to a predetermined program, which will be described later. The quadrangular pyramid mirror 11 is employed for guiding each of the light fluxes in three axes separated into predetermined sections of a single unit of the CCD camera 9, but this is employed as necessary, and another means may be employed instead of the mirror.

In this embodiment, crystal wavelength plates with birefringence phase differences of 79 [nm] and 10 [nm] are used one each as samples to be measured. They are used in order to check whether or not the phase difference γ and the azimuth ϕ can be measured with accuracy in either of large and small birefringence. Product tolerances of the birefringence phase difference of the samples are ±3.5 [nm] and ±4.7 [nm], respectively, and the azimuth of the phase advance axis is known to match a diagonal line of the square crystal wavelength plate. Also, the "azimuth of the phase advance axis" and the "azimuth of birefringence" are used as synonyms here. Similarly, the "birefringence phase difference" and the "size of birefringence" are also used as synonyms.

In an experiment using this embodiment, the phase advance axis of the crystal wavelength plate, which is a sample placed on the sample stand 5, is rotated around the laser optical axis from 0° to 360° by +10°, while the three light intensities $i_1$, $i_2$, $i_3$ are measured, and the birefringence phase difference γ and the phase advance axis azimuth ϕ are acquired using the expression 4, expression 5. Each time this series of operations is carried out once for the above two types of samples, a routine to re-assemble or re-adjust the device in FIG. 8 is repeated. Then, the values $i_1$, $i_2$, $i_3$ of the above three light intensities are sampled approximately in the number of 110 for each sample.

In order to evaluate an influence given by the beam splitter on the birefringence measurement shown in FIG. 8, the above experiment is conducted also in a state where the two beam splitters 6A, 6B are removed from the device and compared.

Since the "accuracy of the phase difference" and the "accuracy of the azimuth", which will be described below, are demonstrated from these experiments, the fact that the birefringence measurement principle of the birefringence measuring device of the present invention is sufficiently correct can be confirmed.

"Accuracy of Phase Difference"

The measurement results of the birefringence phase difference in two samples are shown on the second row, the measurement results of the phase advance axis azimuth on the third row, and the number of measurement times on the fourth row, respectively, in Table 2 shown in FIG. 9. On the first row in Table 2, the birefringence phase difference guaranteed by the manufacturer through management of the sample thickness and machining tolerance is shown. Therefore, the sample should have the birefringence phase difference within this tolerance.

As shown in the first line on the second row in Table 2, average values of the birefringence phase difference γ of the measured two samples are both within the tolerance. The standard deviations of the respective measured values are 3.24 [nm] and 2.62 [nm]. The values in the third line on the second row in Table 2 are results of correction for reducing the fluctuation, which will be described later.

"Accuracy of Azimuth"

The measurement results of the phase advance axis azimuth ϕ of the sample are evaluated according to whether or not the measured value ϕ is increased by 10°. Thus, the closer to 10° the measured value on the third row in Table 2 is, it means that the value is the more accurate. As shown in the first line on the third row in Table 2, average values of the phase advance axis azimuths of the measured two samples are both 10.1°. The standard deviations of the respective measured values are 1.23° and 4.31°. The values in the third line on the third row in Table 2 are results of the correction similar to the above, and the details will be described below.

[Causes of the Fluctuation, Reducing Method and Its Result"

In the device in FIG. 8, factors giving a predominant influence on the fluctuation of the measurement results seem to include the tolerance in the birefringence phase difference in the ¼ wavelength plate 4 and the influence given by the beam splitters 6A, 6B on the measured values. The latter will be described later, and the influence given by the tolerance of the ¼ wavelength plate 4 on the measured values will be explained.

Figure 10:
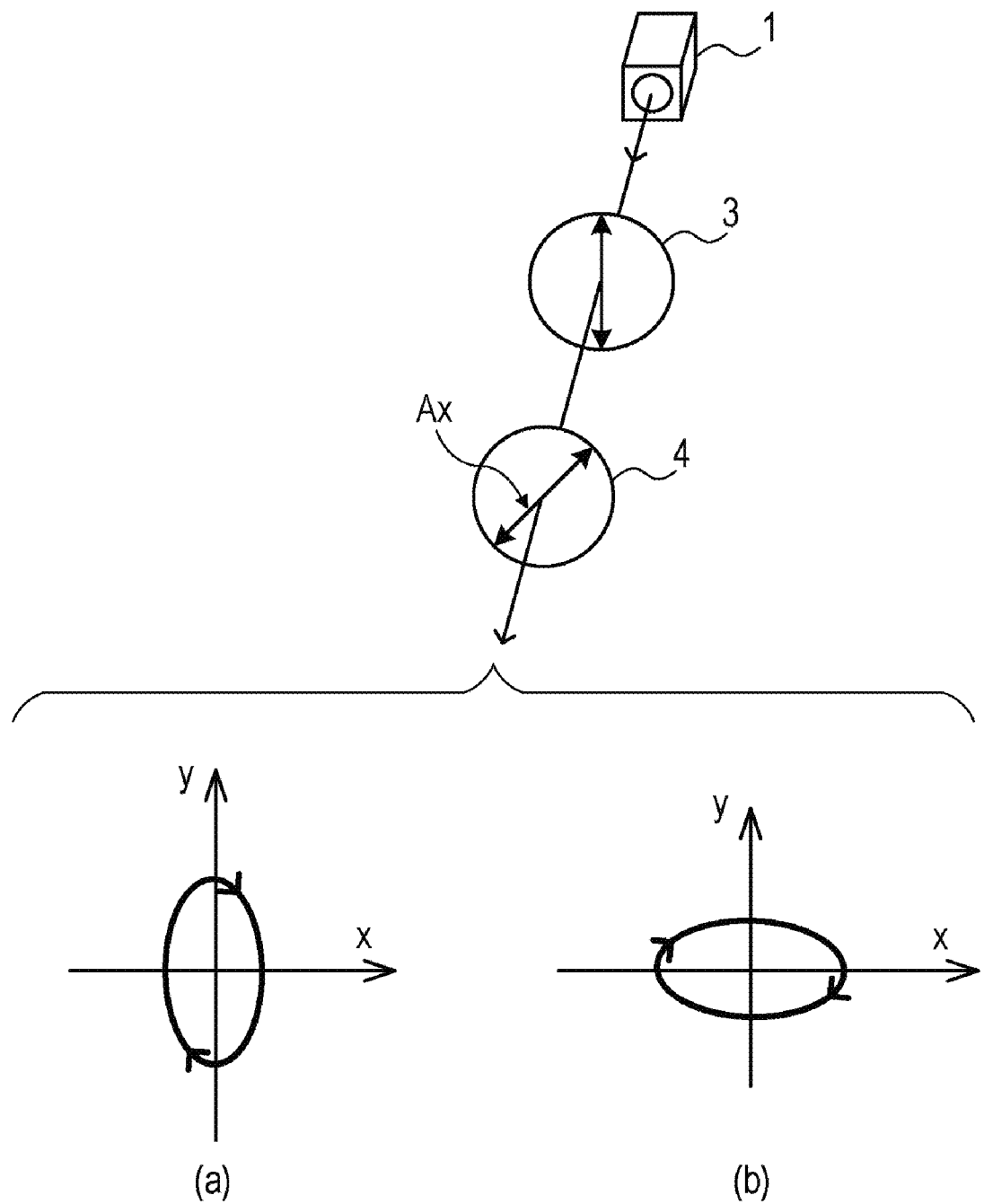
FIG. 10 is an explanatory diagram illustrating a polarization state caused by a product tolerance of a ¼ wavelength plate of a light flux incident to a sample through the ¼ wavelength plate in the embodiment of the present invention.

In the case of the device shown in FIG. 8, the light incident to the object to be measured is preferably circularly polarized light. However, since the ¼ wavelength plate 4 has a micro tolerance, an elliptical polarized light as shown in FIGS. 10A, 10B is considered to enter actually. FIG. 10A shows the elliptical polarization when the birefringence phase difference of the ¼ wavelength plate 4 is less than ¼ wavelength in an exaggerated manner, while FIG. 10B shows the elliptical polarization when the birefringence phase difference of the ¼ wavelength plate 4 exceeds ¼ wavelength on the contrary in the exaggerated manner. Reference character Ax denotes a principal axis.

The fluctuation of the measurement results is considered to be caused by the elliptical polarization. For example, when the elliptical polarization in FIG. 10A enters the sample, the measured birefringence phase difference depends on the phase advance axis azimuth of the sample and vibrates like a sinusoidal wave around a true value. When the phase advance axis azimuth of the sample is 0°, the minimum birefringence phase difference is measured, while when the azimuth is 90°, the maximum birefringence phase difference is measured. Subsequently, it is checked if this fact appears in all the experiment results.

Figure 11:
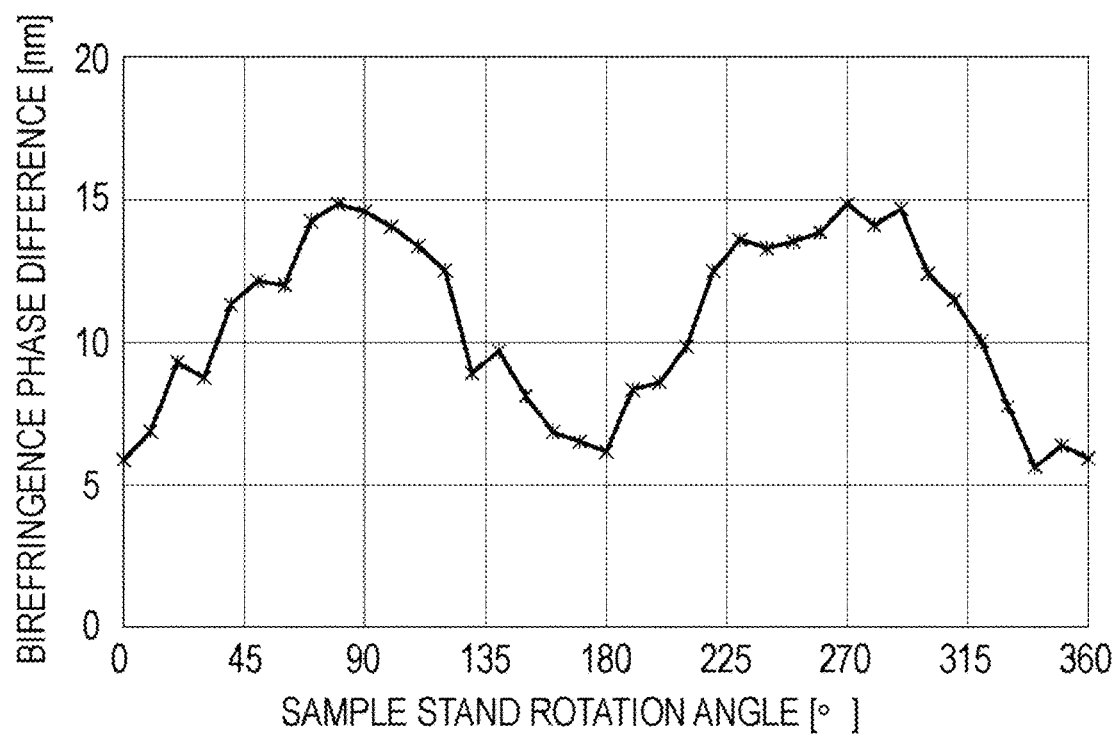
FIG. 11 is a graph illustrating a vibration of a sinusoidal wave pattern of a measured value of a birefringence phase difference caused by the tolerance of the ¼ wavelength plate in the embodiment of the present invention.

FIG. 11 shows typical measurement results of a sample with the birefringence phase difference of 10 [nm]. The lateral axis indicates a rotation angle of the sample stand 5 on which the sample is placed, while the longitudinal axis indicates the measurement result of the birefringence phase difference, respectively. The rotation angle of the sample stand 5 and the phase advance axis azimuth of the sample are matched with each other. The measurement result of the birefringence phase difference γ takes the minimum value when the phase advance axis azimuth is 0°, the maximum value at 90°, and an average value is 10.6 [nm]. Since all the other experiment results have substantially the same tendency, the tolerance of the ¼ wavelength plate 4 is considered to constitute one of factors of the fluctuation in the measured values.

"Reducing Method of the Fluctuation"

Due to the above-mentioned factors, the birefringence having a certain phase difference and azimuth is vector-synthesized with the measured value all the time, and the measured value vibrates like a sinusoidal wave as in FIG. 11. Therefore, it is only necessary to vector-synthesize the birefringence offsetting the fluctuation (hereinafter referred to as compensation birefringence) with the measured value. Then, the phase difference and the azimuth of the compensation birefringence are logically estimated, and vector synthesis is carried out actually so as to search a value at which the standard deviation becomes the minimum. As the method of vector-synthesis, a method described in "Fast Refraction Measurement by Infrared Transverse Zeeman Laser" by Takawa, Umeda, Optics, Vol. 19, No. 7, pp. 464 to 471, July 1990" was employed.

The tolerance of the birefringence phase difference in the ¼ wavelength plate 4 is ±3.5 [nm]. Thus, the phase difference of the compensation birefringence is estimated to be 3.5 [nm] or less. Since the measured value of the birefringence phase difference is the minimum when the azimuth of the sample is substantially 0° in FIG. 11, the azimuth of the compensation birefringence is estimated to be 0°.

Then, supposing that the azimuth of the compensation birefringence is 0°, the phase difference of the compensation birefringence with the standard deviation of all the experiment results shown in Table 2 being the minimum is calculated. As a result, it is known that the standard deviation of all the experiment results becomes the minimum when the phase difference of the compensation birefringence is 3.5 [nm]. Moreover, trial calculation is conducted at 3.5 [nm] or more, and it is confirmed that the standard deviation does not become the minimum.

"Result of Reduction in Fluctuation"

The birefringence phase differences of the two samples are shown on the second row in Table 2 and the phase advance axis azimuths on the third row, respectively. The values shown in italic in the third line on each row in Table 2 are results of the correction to reduce the fluctuation. As shown in the third line on the second row in Table 2, both the average values of the birefringence phase differences $\gamma$ of the two samples are within the tolerance after the correction. Also, the respective standard deviations are 2.61 [nm] and 1.11 [nm], which are decreased by 19.4% and 57.6%, respectively, as compared with the values before the correction.

As shown in the third line on the third row in Table 2, both the average values of the phase advance axis azimuths of the two samples after the correction are 10.0°. Since the sample is rotated by 10°, the value after the correction can be considered as ideal. The respective standard deviations are 0.906° and 3.05°, which are decreased by 26.3% and 29.2%, respectively, as compared with those before the correction.

From the above, effectiveness of the present invention can be confirmed as follows. Using a new birefringence measuring device not requiring either mechanical rotation or electric turning of a polarization face, the phase difference $\gamma$ and the phase advance axis azimuth $\phi$ of the samples with the phase differences of 79.1 nm and 10.0 nm, respectively, are measured approximately 110 times, respectively. As a result, it can be confirmed that the present measuring device that acquires the birefringence phase difference $\gamma$ and the phase advance axis azimuth $\phi$ from the three light intensities $i_1, i_2, i_3$ is appropriate.

Also, as the result of examination of the characteristics of the fluctuation in the measurement results, it is made clear that the tolerance of the ¼ wavelength plate 4 is appropriate as a cause. When the birefringence for the tolerance is compensated in the experiment result, it is confirmed that the standard deviation can be reduced by 57.6% at the maximum and 19.4% at the minimum.

On the other hand, the influence given by the beam splitters 6A, 6B on the birefringence of the sample is checked using a control experiment, but a bad influence by the beam splitter is not detected in the experiment by means of the device of this embodiment.

When the experiment result is compared with the measurement result by means of the birefringence measuring device in FIG. 12, which is a prior art, the finding is as follows. The thesis by Hobbs et al. describes in the middle of the right column on page 408 that the error is 8.8%. As compared with the measurement result of this prior-art example, the error in the present invention is, as shown in the result of the 79.1 nm sample in Table 2, as small as 3.3% (calculated as (2.61/79.1)×100%), which is advantageous. The error of 8.8% in the measurement result by Hobbs et al. is a birefringence measurement error of a disc obtained by stress freezing by giving such a strong stress that a lot of photoelastic fringes appear. On the other hand, the birefringence measurement error of the sample corresponding to 0.5 fringe in the embodiment of the present invention (that is the 79.1 nm sample) is sufficiently small. That is, the phase difference is small and thus, yields a better result even in a situation with a poorer S/N ratio. Thus, effectiveness of the present invention is obvious.

The invention claimed is:

1. A birefringence measuring device for measuring a size of birefringence less than ¼ wavelength existing in an object to be measured and an azimuth thereof, comprising:

a light source configured to emit a light flux having a specific polarization state towards said object to be measured;

an optical system configured to extract each light flux in predetermined three polarization directions from the light flux having passed said object to be measured;

a detector configured to detect a light amount of each of the light fluxes in the predetermined three polarization directions extracted by the optical system; and a processor configured to calculate a size of birefringence of said object to be measured and an azimuth thereof by assigning each light amount of said detected light fluxes detected by the detector to a predetermined function expression, wherein axes of 45°, 0°, and 90°, respectively, are set as the predetermined three polarization directions, and when $i_1, i_2, i_3$ are obtained as the light amounts in each of the predetermined three polarization directions, the processor is configured to calculate the size and the azimuth of the birefringence of said object to be measured by at least one of the following expressions:

$$\phi = \frac{1}{2}\tan^{-1}\left(\frac{i_2 - i_3}{-2i_1 + i_2 + i_3}\right) \quad \text{[Expression B1]}$$

$$\gamma = \sin^{-1}\left(\frac{-2i_1 + i_2 + i_3}{(i_2 + i_3)\cos 2\phi}\right)$$

and $$\phi = \frac{1}{2}\tan^{-1}\left(\frac{i_2 - i_3}{-2i_1 + i_2 + i_3}\right) \quad \text{[Expression B2]}$$

$$\gamma = \sin^{-1}\left(\frac{i_2 - i_3}{(i_2 + i_3)\sin 2\phi}\right).$$

2. The birefringence measuring device according to claim 1, wherein said optical system extracts each light flux in the predetermined three polarization directions by switching and installing three types of analyzers transmitting only each of said predetermined three polarization directions sequentially on the optical path.

3. The birefringence measuring device according to claim 1, wherein said optical system has a beamsplitter configured to divide the light flux having passed said object to be measured into three light fluxes to be detected in a state where the polarization is preserved and three analyzers for extracting a light flux in a predetermined polarization direction from each of said three light fluxes to be detected at the same time.

4. The birefringence measuring device according to claim 1, wherein said object to be measured includes at least one of a semiconductor crystal, a crystal waveplate, an optical element, and a flat display panel.

5. The birefringence measuring device according to claim 1, further comprising:
a polarizer, disposed between the light source and said object to be measured, to align the light flux in the specific polarization state.

6. The birefringence measuring device of claim 1, further comprising:
a quarter waveplate, disposed between the light source and said object to be measured, to transform the specific polarization state to a circular polarization state.

7. A birefringence measuring method for measuring a size of birefringence less than ¼ wavelength existing in an object to be measured and an azimuth thereof, comprising steps of:
emitting a light flux having a specific polarization state to said object to be measured;
having the light flux transmitted through said object to be measured pass through an optical system so as to extract the light flux in each of predetermined three polarization directions;
detecting a light amount of each of the light fluxes in said predetermined three polarization directions extracted by said optical system; and
calculating the size of the birefringence of said object to be measured and the azimuth thereof by assigning the detected light amount of each light flux in said predetermined three polarization directions to a predetermined function expression,
wherein axes of 45°, 0°, and 90°, respectively, are set as said predetermined three polarization directions, and when $i_1, i_2, i_3$ are obtained as light amounts in each of the axial directions, a size and an azimuth of the birefringence of said object to be measured are calculated by at least one of the following expressions:

$$\phi = \frac{1}{2}\tan^{-1}\left(\frac{i_2 - i_3}{-2i_1 + i_2 + i_3}\right) \quad \text{[Expression B1]}$$
$$\gamma = \sin^{-1}\left(\frac{-2i_1 + i_2 + i_3}{(i_2 + i_3)\cos 2\phi}\right) \text{ and}$$

$$\phi = \frac{1}{2}\tan^{-1}\left(\frac{i_2 - i_3}{-2i_1 + i_2 + i_3}\right) \quad \text{[Expression B2]}$$
$$\gamma = \sin^{-1}\left(\frac{i_2 - i_3}{(i_2 + i_3)\sin 2\phi}\right).$$

8. The birefringence measuring method according to claim 7, wherein said object to be measured includes at least one of a semiconductor crystal, a crystal waveplate, an optical element, and a flat display panel.

9. The birefringence measuring method according to claim 7, further comprising:
aligning the light flux in the specific polarization state.

10. The birefringence measuring method according to claim 7, further comprising:
transforming light flux from the specific polarization state to a circular polarization state as the light flux propagates towards said object to be measured.

11. A birefringence measuring method for measuring a size of birefringence less than ¼ wavelength existing in an object to be measured and an azimuth thereof, the method comprising:
emitting a light flux having a specific polarization state to said object to be measured;
having the light flux transmitted through said object to be measured pass through an optical system so as to extract the light flux in each of predetermined three polarization directions;
detecting a light amount of each of the light fluxes in said predetermined three polarization directions extracted by said optical system; and
calculating the size of the birefringence of said object to be measured and the azimuth thereof by assigning the detected light amount of each light flux in said predetermined three polarization directions to a predetermined function expression, wherein
(a) a target object to be measured or an arbitrary object to be measured are used as a test object to be measured, and the test object to be measured is rotated around an optical axis of a light source at least 180° so as to measure the size and the azimuth of the birefringence, a relation between a fluctuation tendency of the birefringence size and the azimuth of the test object to be measured is acquired, a birefringence size γ' and an azimuth φ' causing the fluctuation tendency are estimated, and the birefringence offsetting it is set as compensation birefringence r';
(b) said compensation birefringence r' is vector-synthesized with the measurement result of said test object to be measured so as to acquire the relation between the fluctuation tendency of the size and the azimuth of the birefringence again, and a standard deviation of the birefringence size of said test object to be measured from the relation;
(c) by changing said birefringence size γ' and the azimuth φ' as appropriate, the compensation birefringence r' acquired from the size γ' and the azimuth φ' of the birefringence after the change is vector-synthesized again with the measurement result of the test object to be measured so as to re-acquire the relation between the fluctuation tendency of the size and the azimuth of the birefringence, and the standard deviation of the size of the birefringence of said test object to be measured is acquired from the relation;
(d) the processing in the above (c) is repeated so as to search the size γ' and the azimuth φ' of the birefringence at which the standard deviation of the size of the birefringence of said test object to be measured is the minimum, and the birefringence obtained as the result of the search is set as final compensation birefringence r";
(e) the final compensation birefringence r" obtained by the processing in the above (d) is set as a calibration value;
(f) the size γ and the azimuth φ of said birefringence of said target object to be measured are measured, and the birefringence r is acquired from the measurement result; and
(g) the final compensation birefringence r" obtained by the processing in the above (d) is vector-synthesized with the birefringence r obtained by the processing in the above (f) so as to obtain compensated birefringence $r_{real}$, and vector components of the compensated birefringence $r_{real}$ are obtained as the size $\gamma_{real}$ and the azimuth $\phi_{real}$ of the true birefringence of said object to be measured from which a tolerance of the measurement system is eliminated.

12. The birefringence measuring method according to claim 11, wherein said object to be measured includes at least one of a semiconductor crystal, a crystal waveplate, an optical element, and a flat display panel.

13. The birefringence measuring method according to claim 11, further comprising:
  aligning the light flux in the specific polarization state.

14. The birefringence measuring method according to claim 11, further comprising:
  transforming light flux from the specific polarization state to a circular polarization state as the light flux propagates towards said object to be measured.

15. A birefringence measuring device for measuring a size of birefringence less than ¼ wavelength existing in an object to be measured and an azimuth thereof, comprising:
  a light source configured to emit a light flux having a specific polarization state towards said object to be measured;
  an optical system configured to extract each light flux in predetermined three polarization directions from the light flux having passed said object to be measured;
  a detector configured to detect a light amount of each of the light fluxes in said predetermined three polarization directions extracted by said optical system; and
  a processor configured to calculate a size γ and an azimuth φ of said object to be measured by assigning each light amount of said detected light fluxes detected by the detector to a predetermined function expression,
  wherein a target object to be measured or an arbitrary object to be measured are used as a test object to be measured, and the test object to be measured is rotated around an optical axis of the light source at least 180° so as to measure the size γ and the azimuth φ of the birefringence,
  wherein the processor is further configured:
    to acquire a relation between a fluctuation tendency of the birefringence size and the azimuth of the test object to be measured;
    to estimate a birefringence size γ' and an azimuth φ' causing the fluctuation tendency;
    to set a birefringence offsetting as a compensation birefringence r';
    to vector-synthesize said compensation birefringence r' with the measurement result of said test object to be measured so as to acquire the relation between the fluctuation tendency of the size and the azimuth of the birefringence again, and a standard deviation of the birefringence size of said test object to be measured from the relation;
    to re-acquire the relation between the fluctuation tendency of the size and the azimuth of the birefringence, and the standard deviation of the size of the birefringence of said test object to be measured is acquired from the relation by changing said birefringence size γ' and the azimuth φ' as appropriate, said compensation birefringence r' acquired from the size γ' and the azimuth φ' of the birefringence after the change is vector-synthesized again with the measurement result of the test object to be measured;
    to search the size γ' and the azimuth φ' of the birefringence at which the standard deviation of the size of the birefringence of said test object to be measured is the minimum, and to set the birefringence obtained as the result of the search as a final compensation birefringence r'';
    to set the final compensation birefringence r'' as a calibration value; and
    to vector-synthesize the final compensation birefringence r'' with the birefringence r so as to obtain compensated birefringence $r_{real}$, and vector components of the compensated birefringence $r_{real}$ as the size $\gamma_{real}$ and the azimuth $\phi_{real}$ of the true birefringence of said object to be measured from which a tolerance of the measurement system is eliminated.

16. The birefringence measuring device according to claim 15, wherein said optical system extracts each light flux in said predetermined three polarization directions by switching and installing three types of analyzers transmitting only each of said predetermined three polarization directions sequentially on the optical path.

17. The birefringence measuring device according to claim 15, wherein said optical system has a beamsplitter configured to divide the light flux having passed said object to be measured into three light fluxes to be detected in a state where the polarization is preserved and three analyzers for extracting a light flux in a predetermined polarization direction from each of said three light fluxes to be detected at the same time.

18. The birefringence measuring device according to claim 15, wherein said object to be measured includes at least one of a semiconductor crystal, a crystal waveplate, an optical element, and a flat display panel.

19. The birefringence measuring device according to claim 15, further comprising:
  a polarizer, disposed between the light source and said object to be measured, to align the light flux in the specific polarization state.

20. The birefringence measuring device of claim 15, further comprising:
  a quarter waveplate, disposed between the light source and said object to be measured, to transform the specific polarization state to a circular polarization state.

* * * * *

UNITED STATES PATENT AND TRADEMARK OFFICE
CERTIFICATE OF CORRECTION

Page 1 of 1

PATENT NO. : 8,279,439 B2
APPLICATION NO. : 12/439441
DATED : October 2, 2012
INVENTOR(S) : Gomi It is certified that error appears in the above-identified patent and that said Letters Patent is hereby corrected as shown below:

On the Face Page, in Field (57), under "ABSTRACT", in Column 2, Line 8, delete "direction; and," and insert -- direction --, therefor.

In Column 10, Line 30, delete "the processing" and insert -- The processing --, therefor.

In Column 12, Line 13, delete "[Causes" and insert -- "Causes --, therefor.

Signed and Sealed this
Nineteenth Day of March, 2013

Teresa Stanek Rea
*Acting Director of the United States Patent and Trademark Office*